United States Patent [19]

Sprunt et al.

[11] Patent Number: 4,688,238

[45] Date of Patent: Aug. 18, 1987

[54] METHOD FOR DETERMINING LITHOLOGICAL CHARACTERISTICS OF A POROUS MATERIAL

[75] Inventors: Eve S. Sprunt, Farmers Branch, Tex.; Neil V. Humphreys, Essex, Great Britain; Ernest L. Muegge, Grand Prairie; James R. Dixon, Jr., Dallas, both of Tex.

[73] Assignee: Mobil Oil Corporation, New York, N.Y.

[21] Appl. No.: 868,487

[22] Filed: May 30, 1986

[51] Int. Cl.$^4$ .................. G01N 23/00; G01N 23/04; G01N 15/08

[52] U.S. Cl. .................. 378/4; 378/62; 378/210; 73/38

[58] Field of Search .................. 378/4, 62, 210, 58; 73/38

[56] References Cited

U.S. PATENT DOCUMENTS

| | | | |
|---|---|---|---|
| 4,157,472 | 6/1979 | Beck, Jr. et al. | 250/445 T |
| 4,283,629 | 8/1981 | Habermehl et al. | 250/445 T |
| 4,399,509 | 8/1983 | Hounsfield | 364/414 |
| 4,422,177 | 12/1983 | Mastronardi et al. | 378/17 |
| 4,599,891 | 7/1986 | Brauer et al. | 73/38 |

OTHER PUBLICATIONS

"Computed Tomographic Analysis of Meteorite Inclusions", by J. R. Arnold et al., *Science*, vol. 219, Jan. 1983, pp. 383–384.

*Primary Examiner*—Carolyn E. Fields
*Assistant Examiner*—Joseph A. Hynds
*Attorney, Agent, or Firm*—Alexander J. McKillop; Michael G. Gilman; George W. Hager, Jr.

[57] ABSTRACT

A substantially cylindrical sample of a porous material is surrounded by an elastic jacket and placed in a confining pressure cell. Pressure is supplied to the cell to press the jacket into contact with the surface of the sample. The pressure is varied over a plurality of pressure points and is scanned at a plurality of locations with X-rays at each such pressure point. A computed tomographic image is produced for each X-ray scan. Conformance of the jacket to the sample is determined from these computed tomographic images and a range of confining pressure is determined over which parameters of the sample may be measured without being affected by improper conformance of the jacket to the surface of the sample. The sample structure is monitored with these tomographic images for fractures produced due to the increase of pressure. The fracture starting point is determined to be interior or surface related.

8 Claims, 3 Drawing Figures

METHOD FOR DETERMINING LITHOLOGICAL CHARACTERISTICS OF A POROUS MATERIAL

BACKGROUND OF THE INVENTION

In the production of minerals, e.g., oil and gas, certain lithological properties of a subterranean reservoir must be determined. Two of the most important of these properties are the porosity and permeability of the reservoir. Porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. Permeability of a material is a measure of the ability of the material to transmit fluids through its pore spaces and is inversely proportional to the flow resistance offered by the material. Another important parameter is pore compressibility, which is change in porosity, or pore and bulk volume, as a function of pressure.

Normally, these parameters are determined by taking core samples from the reservoir and carrying out well-defined measurement techniques on the samples. There are several techniques available for making such measurements, many of which are described in *PETROLEUM PRODUCTION ENGINEERING—DEVELOPMENT* by L. C. Uren, Fourth Edition, McGraw-Hill Book Company, Inc., 1956, pps. 660–669. Another standard reference is American Petroleum Institute, *API Recommended Practice for Core-Analysis Procedure*, API RP 40, 1960, 55 pp.

A more recently applied technique involves computed tomography (CT) technology which has been in use in the medical field for a number of years. CT scanning instruments produce a cross-sectional view through the subject material along any chosen axis. The advantages of CT scanning over conventional radiography is found in its ability to display the electron density variations within the object scanned in a two-dimensional X-ray image. In medical CT scanners, an X-ray source and a detector array circle a patient in a period of about 2 to 9 seconds and produces an image with maximum resolutions of 0.25 mm in the X-Y plane. This plane can be moved in discrete intervals to obtain information in three dimensions. For more details of such medical CT scanners, reference may be made to U.S. Pat. No. 4,157,472 to Beck, Jr. and Barrett (Assignee: General Electric Company) and U.S. Pat. No. 4,399,509 to Hounsfield (Assignee: EMI Limited).

Many other applications of CT scanning can also be made. For example, in an article entitled, "Computed Tomographic Analysis of Meteorite Inclusions", *Science*, pps. 383–384, Jan. 28, 1983, there is described the non-destructing testing of meteorites for isotopic anomalies in calcium- and aluminum-rich inclusions of heterogeneous materials, such as Allende. The CT scanning equipment described in such article is the Deltascan 2020 from Technicare. In a further application, CT scanning has been applied to the non-destructive testing of wood materials, such as for disease in living trees, see U.S. Pat. No. 4,283,629 to Habermehl. In a yet further application, CT scanning has been applied to the examination of non-living objects, such as motors, ingots, pipes, etc., see U.S. Pat. No. 4,422,177 to Mastronardi, et al. (Assignee: American Science and Engineering, Inc.).

More recently, the CT scanning technology has been applied to the field of energy research for examining the interior of stationary or slowly changing earth materials, such as coal, shale and drilling cores. Processes involved in coal gasification and combustion have been monitored using time-lapse CT imagery to observe changes in density (e.g., thermal expansion, fracturing, emission of gases, consumption by combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid fronts. By subtracting the images of the cores before and after flooding, the exact shapes of the fluid front was determined. Such core flood experiments allows the interior of the core sample to be observed without disturbing the sample. The sweep efficiency and flow paths of fluids of interest may now be studied on the scale of millimeters. The penetration of X-rays allows experiments to be performed with up to 4-inch diameter core samples.

Drilling fluids can be analyzed by CT scanning as such fluids are characterized by high-density brines, various organics and several compositionally different weighting agents. Formation damage can be investigated since CT scanning can detect migration of clays, absorption of organics and the reversibility of completion fluid penetration. Shale oil recovery can be aided as CT scanning could detect penetration by solvents and could directly measure structure changes on retorting. Rock fractures can be identified.

SUMMARY OF THE INVENTION

This invention is directed to a method for determining the range of confining pressures which can be applied to an elastic jacket surrounding a substantially cylindrical sample of a porous material during a measurement of the lithological characteristics of the porous material such as pore compressibility, porosity or permeability. The sample, with its surrounding elastic jacket, is placed in a confining pressure cell. Pressure is applied to the cell to press the jacket into contact with the surface of the sample. The pressure in the cell is varied over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which parameters of the sample may be measured without being affected by improper conformance of the jacket to the surface of the sample.

In one aspect of the invention, the upper limit of the range of pressure points of the pore compressibility measurement for which no corrections for jacket conformance is needed is selected as that pressure at which intrusion of the jacket into the near surface pores of the sample causes a pore volume measurement that is lower than the actual pore volume of the sample, while the lower limit is selected as that pressure at which loosening of the conformance of the jacket around the sample causes a pore volume measurement that is greater than the actual pore volume of the sample.

Another aspect of the invention is using consecutive computed tomography scans to image the entire sample to calculate the pore volume occupied by an improperly conforming jacket. This procedure would raise the upper limit for which valid pore volume measurements could be obtained.

In a yet further aspect of the invention, the upper limit of the range of pressure points is selected as that pressure at which crushing of the sample destroys permeable channels within the sample and results in a permeability measurement that is lower due to fracturing rather than reversible closure of pore channels of the sample, while a lower limit is selected as that pressure at which fluid channeling between the jacket and the sample results in a permeability measurement that is greater than the actual permeability of the sample. This observation would determine the crushing pressure of the sample.

The determination of the pore and bulk volume measurement range yields a valid range for pore compressibility measurement.

DESCRIPTION OF THE PREFERRED EMBODIMENT

Figure 1:
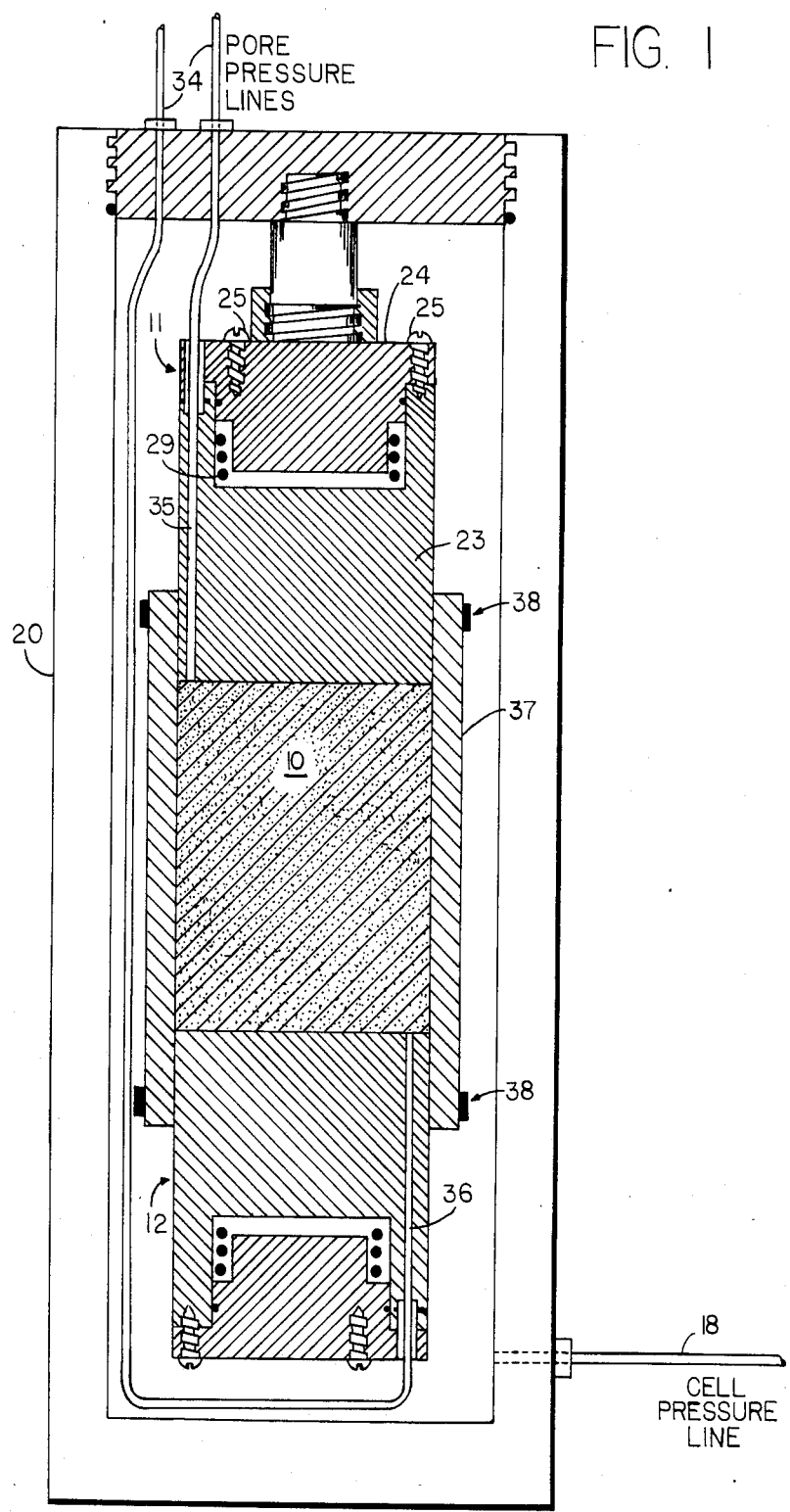
FIG. 1 is a cross-sectional view of a confining pressure cell housing a sample of porous material to be examined in accordance with the method of the present invention.

Referring now to FIG. 1, a sample 10 of a porous material, such as a core sample of a subterranean earth formation, to be examined in accordance with the present invention is mounted between a housing 11 and a housing 12 and is enclosed within a confining pressure cell 20 for subjecting the core sample to varying pressure conditions. The confining pressure condition within the cell 20 is established by the cell pressure line 18.

Housing 11 comprises an annular member 23 and a cover member 24. Such cover member 24 encloses the open end of the annular member 23 and is secured by screws 25. The face of the member 23 is maintained in good contact with the core sample 10 through spring-loading provided by one or more spring-like members 29.

Pore pressure lines 34 provide the desired fluid pressure to the core sample 10 by way of the passageways 35 and 36 in the housings 11 and 12, respectively.

The core sample 10 and portions of housings 11 and 12 are surrounded by a jacket, or sleeve, 37 which may be made of an impermeable elastic material, such as rubber, for example. The jacket 37 is secured to the housings 11 and 12 and the core sample 10 by the clamps 38.

Figure 2:
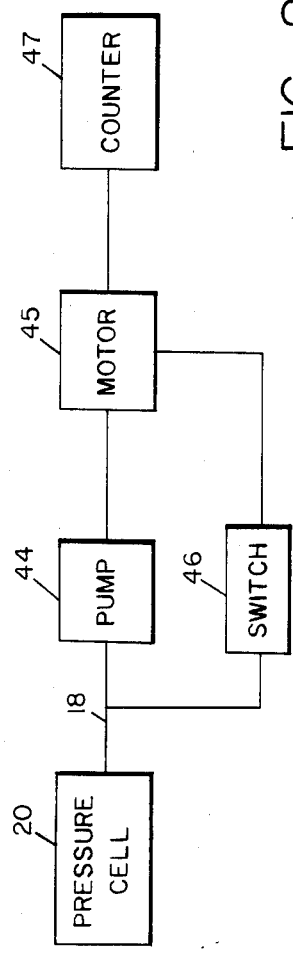
FIG. 2 is a block diagram of the system for supplying confining pressure to the pressure cell of FIG. 1.

The confining pressure applied to cell 20 through cell pressure line 18 is supplied by the system illustrated in FIG. 2. Line 18 is connected to pump means 44 which is operated by motor 45. Pump means 44 is of the type which allows accurate measurement of the amount of fluid pumped, e.g., a screw-feed, positive-displacement pump which has a capacity forward of its displacement piston sufficient to store the volume of non-compressible fluid necessary for use in the present invention. This negates the need for the separate fluid reservoir as is well understood by those skilled in the art, although such a reservoir could be easily provided. Motor 45 is preferably of the type commonly referred to as a stepping motor so that it moves pump means 44 in discrete increments to force non-compressible fluid through pressure supply line 18 into cell 20 to expand jacket 37 into contact with core sample 10. The pressure within the cell 20 may be varied over a plurality of pressure points. A counter 47 records the number of steps of motor 45. Pressure-sensitive switch 46 is connected into pressure supply line 18 to shut off motor 45 when a preset pressure has been reached. By counting the number of steps of motor 45 and knowing the corresponding displacement of pump 44 for each step, the exact amount of fluid which is necessary to reach the preset pressure can be determined. Upon installing the core sample in the pressure cell 20 of FIG. 1 and connecting the confining pressure line from the system of FIG. 2, the pressure cell 20 is placed into the computed tomographic (CT) scanning system illustrated in FIG. 3.

Figure 3:
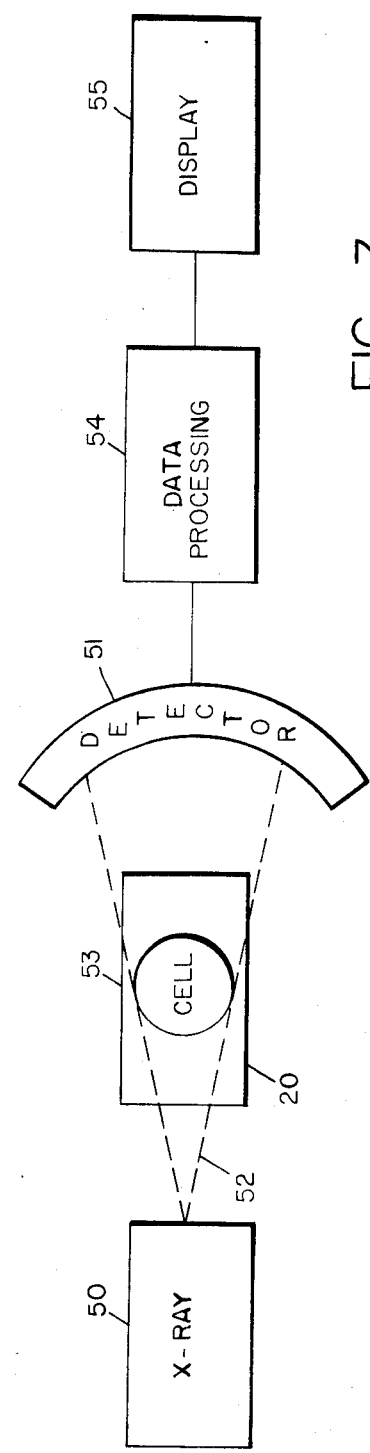
FIG. 3 is a pictorial view of a CT scanning system for use in scanning the sample of porous material in the confining pressure cell of FIG. 1 with X-rays in accordance with the method of the present invention.

Referring now to FIG. 3, X-ray energy provided by the X-ray tube 50 passes through the core sample 10 within the pressure cell 20 and falls on the detector array 51. Rotation of the pressure cell within the X-ray fan beam 52 is provided by the gantry 53. In an alternative embodiment, the core sample 10 may remain stationary and the gentry may be used to rotate the X-ray tube 50 and detector 51 about the core sample. In medical applications, CT scanning rates are usually in the order of 2 to 9 seconds. However, patient dose limitations are of no concern in the present application, and scan times of the core sample can be up to 1 minute per scan, or even longer, if desired. The output of the detector array 51 is passed through the data processing unit 54 to the display unit 55. After a desired number of scans are completed for a core sample slice, the sample is indexed one slice-width through the X-ray fan beam to place the next adjacent sample slice within the path of the X-ray fan beam. In this manner, a 3-D tomographic presentation is made on the display unit 55 of the entire sample by compositing the cross-sectional view of each of the scan slices. Such a CT scanning system, while not forming a part of the present invention, is used in accordance with the method of the present invention to determine the conformance of the jacket 37 to the surface of the core sample 10 under varying pressure conditions.

For a more detailed description of CT scanning systems which may be utilized in the method of the present invention, reference may be made to each of the aforementioned U.S. patents and the referenced *Science* article, the teachings of which are incorporated herein by reference. A particularly suitable detector array 51 for use in the present invention for a 100 micron resolution would comprise a 1024×1 linear array of photodiodes on a 0.001 inch center-to-center spacing with pixel (picture element) aperatures of 0.001 inch by 0,1 inch. An example of such an array is the Reticon 1024S/fiber optic faceplate. For a lower 250 micro resolution, a 200×1 linear array of photodiodes on a 0.01 inch center-to-center spacing with pixel aperatures of 0.01 inch to 0.1 inch would be suitable. An example of such an array is that used in digital mammography equipment supplied by Bio-Imaging Research, Inc. Optically coupled to the input surfaces of the photodiode arrays are scintillation arrays comprised of a plurality of discrete scintillators having X-ray sensitive fluorescent materials individually and optically coupled to the input surfaces of the discrete photodiodes. Such materials may comprise $CdWO_4$, $C_5I$, GdOBr or LaOBr, among others. Such combination of scintillators and photodiodes provides for a complete scintillation counter. The photodiodes provide electrical signals whose heights are proportional to the X-ray energy falling upon the surfaces of the scintillators. After suitable amplification, the signals are digitized for use in producing the desired tomographic display. The fan beam of such X-ray energy is identified by the dashed lines 52 in FIG. 3 as falling upon the detector array 51 after having passed through the core sample 20.

Having completed the installation of the confining pressure cell 20 in the CT scanning system, the method of the present invention for determining the range of confining pressures which can be applied to the elastic jacket surrounding the sample of porous material with the pressure cell during a measurement of the lithological characteristics of the sample, such as pore compressibility, porosity or permeability, now be carried out. Sufficient confining pressure is applied to the cell to press the elastic jacket into contact with the surface of the sample. The pressure is then varied through a plurality of pressure points. The sample is scanned with X-rays at a plurality of locations for each of the pressure points. For greatest accuracy, images should be taken in consecutive slices so that the entire volume of the sample is scanned. A computed tomographic image of the sample is produced for each of the X-ray scans. The conformance of the jacket to the sample is determined from these computed tomographic images. From such conformance, a range of confining pressures is determined over which parameters of the sample may be measured without being affected by improper conformance of the jacket to the surface of the sample.

Improper conformance of the jacket to the surface of the sample may be corrected by using the plurality of computed tomographic images to calculate the pore volume being occupied by the improperly conforming jacket. If the bulk volume were to be measured independently of the pore volume by a measurement of the confining pressure cell, the computed tomographic images would indicate when apparent changes in bulk volume were actually due to improper jacket conformance. The confining pressure cell would have to be calibrated with an incompressible sample in place. The change in bulk volume would be the difference at any given pressure point between the confining pressure cell volume with the porous sample in place and the calibration measurement if no improper jacket conformance existed.

With pore and bulk volume being a function of pressure for some rocks at low confining pressures of 50 to 400 psi, for example, these pressure effects will be difficult to distinguish from jacketing effects. Examples of such rocks are unconsolidated or fractured rocks. It is, therefore, one aspect of the invention to select the lower limit of the range of pressure points as that pressure at which the jacket conforms to the rock. At lower pressures, non-conformance of the jacket causes a pore volume measurement that is higher than the actual pore volume of the sample, while the upper limit is selected as that pressure at which intrusion of the jacket into near surface pores of the sample causes a pore volume measurement that is lower than the actual pore volume of the sample.

In a further aspect, the upper limit of the range of pressures is selected as that pressure at which crushing of the sample destroys or alters permeable channels within the sample and results in a permeability of the sample that is different than the uncrushed sample due to non-reversible fracturing of the pore channels. The lower limit is selected as that pressure at which fluid channeling between the jacket and the sample results in a permeability measurement that is greater than the actual permeability of the sample.

In a still further aspect, the upper limit of the range of pressure points may be selected as that pressure at which fracture is initiated in the near surface or other pores inertia locations of the sample. The location of the fracture origin is critical to determining if the fracture is a surface phenomena or should be applied to the entire rock formation.

In a yet further aspect, the upper limit of the range of pressure points may be selected as that pressure, at which intrusion of the jacket into near surface voids of the sample results in a pore compressibility that is greater than the actual pore compressibility of the sample. Such pore compressibility is determined from the change in pore and bulk volumes. The selection of this upper limit will prevent change in pore volume due to jacket displacement which would otherwise be interpreted falsely as pore compressibility.

While preferred embodiments of the present invention have been described, numerous modifications and alterations may be made without departing from the spirit and scope of the invention as set forth in the appended claims.

We claim:

1. A method for determining the range of confining pressures which can be applied to an elastic jacket surrounding a substantially cylindrical sample of a porous material during a measurement of the lithological characteristics of said sample of porous material, comprising the steps of:
   (a) placing said sample with its surrounding elastic jacket in a confining pressure cell,
   (b) supplying pressure to said cell to press said jacket into contact with said sample,
   (c) varying the pressure within said cell over a plurality of pressure points,
   (d) scanning said sample with X-rays at a plurality of locations at each of said pressure points,
   (e) producing computed tomographic images of said sample for each of said plurality of locations and said pressure points,
   (f) determining from said computed tomographic images the conformance of said jacket to the surface of said sample at each of said pressure points, and
   (g) determining from said conformance a range of pressures for said confining pressure over which sample parameters may be measured without being affected by improper conformance of said jacket to the surface of said sample.

2. The method of claim 1 wherein the upper limit of said range of pressure points is selected at that pressure at which fracture is initiated in said sample, as determined from said computed tomography images.

3. The method of claim 2 further including the step of determining from said computed tomography images if said fracture occurs in the near surface pores of said sample or in the interior of said sample.

4. The method of claim 1 wherein:
   (a) the upper limit of said range of pressure points is selected as that pressure at which intrusion of said jacket into the near surface pores as determined from said computed tomography images of said sample results in a pore volume measurement that is lower than the actual pore volume of said sample, and
   (b) the lower limit of said range of pressure points is selected as that pressure at which loosening of the conformance of said jacket as determined from said computed tomography images around said sample results in a pore volume measurement that is greater than the actual pore volume of said sample, and
   (c) measuring the pore volume of said sample over said range of pressure points.

5. The method of claim 1 wherein:
   (a) the upper limit of said range of pressure points is selected as that pressure at which crushing of said sample as determined from said computed tomography images destroys or alters permeable channels within said sample and results in a permeability measurement that is different than the actual permeability of said sample, due to inelastic fracturing,
   (b) the lower limit of said range of pressure points is selected as that pressure at which fluid channeling between said jacket and said sample results in a permeability measurement that is greater than the actual permeability of said sample, and
   (c) measuring the permeability of said sample over said range of pressure points.

6. The method of claim 1 wherein:
   (a) the upper limit of said range of pressures is selected as that pressure at which intrusion of said jacket into near surface voids of said sample as determined from said computed tomography images results in a pore compressibility measurement from pore and bulk volume, that is greater than the actual pore compressibility of said sample, and
   (b) measuring the pore compressibility of said sample over a range of pressures that does not exceed said upper limit.

7. The method of claim 1 further comprising the step of correcting for improper conformance of said jacket to the surface of said sample by using a plurality of computed tomographic images to calculate the pore volume occupied by an improperly conforming jacket.

8. The method of claim 1 further comprising the step of correcting for improper conformance of said jacket to the surface of said sample by, firstly, calibrating said confining pressure cell with an incompressible sample being in place within said cell and, secondly, measuring the change in pore volume of said sample when said sample is in place within said cell as a function of pressure.

* * * * *